US011510815B2

(12) United States Patent
Marconi (10) Patent No.: US 11,510,815 B2
(45) Date of Patent: Nov. 29, 2022

(54) GOGGLE

(71) Applicant: RUROC IP HOLDINGS LIMITED, Gloucester (GB)

(72) Inventor: Matteo Marconi, Gloucester (GB)

(73) Assignee: RUROC IP HOLDINGS LIMITED, Gloucester (GB)

( * ) Notice: Subject to any disclaimer, the term of this patent is extended or adjusted under 35 U.S.C. 154(b) by 0 days.

(21) Appl. No.: 16/962,495

(22) PCT Filed: Apr. 25, 2018

(86) PCT No.: PCT/EP2018/060609
§ 371 (c)(1),
(2) Date: Jul. 15, 2020

(87) PCT Pub. No.: WO2019/137632
PCT Pub. Date: Jul. 18, 2019

(65) Prior Publication Data
US 2021/0077301 A1 Mar. 18, 2021

(30) Foreign Application Priority Data
Jan. 15, 2018 (GB) .................................... 1800635

(51) Int. Cl.
*A61F 9/02* (2006.01)
(52) U.S. Cl.
CPC .................... *A61F 9/025* (2013.01)
(58) Field of Classification Search
CPC ............. A61F 9/02; A61F 9/025; A61F 9/028
(Continued)

(56) References Cited

U.S. PATENT DOCUMENTS

2004/0083540 A1* 5/2004 Dondero ................. A61F 9/027
2/436
2009/0313746 A1 12/2009 Wang
(Continued)

OTHER PUBLICATIONS

European Patent Office (EPO); International Search Report for International Patent Application PCT/EP2018/060609, dated Oct. 16, 2018, EPO, The Hague, Netherlands.

*Primary Examiner* — F Griffin Hall
(74) *Attorney, Agent, or Firm* — Nevin Carmichael Consulting (57) ABSTRACT

A goggle for use in snowsports comprises a body (14) and a detachable lens assembly (12), magnets or magnetic elements being provided on the lens assembly (12) and magnets or magnetic elements being provided in corresponding positions on the body (14), for detachably holding the lens assembly (12) to the body (14), at least one tongue (34) extending from the rear surface (36) of the lens assembly (12) on each lateral side (18, 54) of the lens assembly (12), each tongue (34) extending in a direction substantially behind the lens assembly (12), into the body (14) when the lens assembly (12) is fitted to the body (14), and an aperture (42, 66) extending through each tongue (34), and at least one moveable clip (72) being provided on each lateral side (18, 54) of the body (14), each clip (72) being movable between a released position and an engaged position, each clip (72) including a retaining finger (82) which in the engaged position passes into the aperture (42, 66) in the tongue (34), preventing detachment of the lens assembly (12) from the frame and in the released position moves clear of the tongue (34), allowing detachment of the lens assembly (12).

14 Claims, 8 Drawing Sheets

(58) Field of Classification Search
USPC .............................. 2/426, 431, 435, 436, 437
See application file for complete search history.

(56) References Cited

U.S. PATENT DOCUMENTS

| | | |
|---|---|---|
| 2012/0038879 A1 | 2/2012 | Reyes |
| 2013/0104300 A1* | 5/2013 | Park ........................ A61F 9/025 |
| | | 2/439 |
| 2015/0124211 A1 | 5/2015 | Park |
| 2016/0287444 A1 | 10/2016 | Han |
| 2017/0128267 A1 | 5/2017 | Rees |
| 2017/0216098 A1* | 8/2017 | Li ........................... A61F 9/025 |

* cited by examiner

GOGGLE

The present invention relates to a goggle for use in snowsports.

BACKGROUND TO THE INVENTION

Goggles are worn in snowsports to protect the eyes from wind and bright light, such as sunlight reflected off snow. Such goggles typically comprise a frame, which is strapped to the face of the wearer, and a lens which sits within the frame.

Lenses are available in different tints and colours, and different lenses are designed for optimal performance in different weather conditions. A skier who skis in a range of different conditions will therefore want a range of different lenses. To avoid the bulk and expense of multiple pairs of goggles, goggles with interchangeable lenses are preferred, and preferably the lens is able to be swapped over as quickly and easily as possible.

Existing interchangeable lens systems include, for example, clips, magnets, or other releasable retaining means to keep the lens in place on the frame of the goggle. However, existing quick release mechanisms generally require a clip to be unfastened before the lens can be removed, which can be difficult to do quickly, especially while the goggles are being worn.

Prior art clips generally overlie a portion of the lens to retain the lens on the frame. A pulling motion is therefore required to move the clip away from the lens. It can be difficult to get a grip on the clip, which is likely to be small, if the hands are gloved or partially numb due to cold.

Another problem with clips that overlie a part of the lens is that they reduce the aesthetic appeal of the goggles by complicating the external appearance.

It is an object of the invention to reduce or substantially obviate the above mentioned problems.

STATEMENT OF INVENTION

According to a first aspect of the present invention, there is provided a goggle for use in snowsports, the goggle comprising a body and a detachable lens assembly, magnets or magnetic elements being provided on the lens assembly and magnets or magnetic elements being provided in corresponding positions on the body, for detachably holding the lens assembly to the body, at least one tongue extending from a rear surface of the lens assembly on each lateral side of the lens assembly, each tongue extending in a direction substantially behind the lens assembly, into the body when the lens assembly is fitted to the body, and an aperture extending through each tongue, and at least one moveable clip being provided on each lateral side of the body, each clip being movable between a released position and an engaged position, each clip including a retaining finger which in the engaged position passes into the aperture in the tongue, preventing detachment of the lens assembly from the frame and in the released position moves clear of the tongue, allowing detachment of the lens assembly.

The magnets attract and hold the lens to the body, making the lens easy to replace on the body as it is guided into position by the magnets. The tongue and movable clip engage to securely hold the lens to the body so that it is not easily knocked off in a fall or collision, with the fingers holding the tongue to the body. The situation of the tongues behind the lens and their orientation into the body means that the clip does not have to overlie a portion of the lens to hold the lens to the body, but can rather be situated substantially behind the lens adjacent to the tongues. This allows the clip to be moved from the engaged to the released position by pushing the clips inwardly, i.e. towards the wearer's head, without pulling on the clip, which can be fiddly and difficult. A front face may be provided on each clip to facilitate pushing and avoid the need to grip on an edge of a clip.

A bearing surface may be provided on the body for positioning adjacent to each tongue. The body of the goggles may be flexible to improve resilience to fracture in an impact, and this may allow slight movement between the lens and the body in use. The bearing surface prevents the tongues from sliding off the fingers as a result of this movement. The fingers sit opposite the bearing surfaces with the clearance between the ends of the fingers and the bearing surfaces being smaller than a thickness of the tongues, so that the tongues cannot pass between the fingers and the bearing surfaces.

An aperture may be provided in the body for receiving each tongue. The walls of the aperture can then act as the above-mentioned bearing surfaces.

Each finger may be situated in one of the apertures when the clip is in the engaged position. The fingers hold the tongues in the apertures as discussed above.

Each aperture may be situated near a lateral edge of the body. This is so as to receive the tongues, which are situated near lateral edges of the lens assembly.

A channel may be provided joining each aperture to the respective lateral edge of the body, each channel being open to front and side surfaces of the body for receiving one of the retaining fingers. This allows the fingers to pass from the apertures to the lateral edge of the body, where the remainder of the clip may be situated, without obstructing the lens assembly, so that the lens assembly can sit on the front of the body and the magnetic elements can approach closely.

Each movable clip may be hinged to the body. This provides a simple mechanism for moving the clip between the engaged and released positions and allows a pushing motion to be used to move the clip, which is easier to execute than having to grip on an edge and pull.

Each moveable clip may include an actuating portion for actuating the moveable clip by pushing.

Each movable clip may comprise an elongate bar portion disposed parallel to the respective lateral edge. The bar portion provides a body for the clip and a surface which can be pushed to move the clip from the engaged position to the released position. It provides a low-profile body on which multiple fingers can be provided.

Pushing the actuating portion towards the body of the lens may cause the clip to move from the engaged position to the released position.

The clip may be pivotable about the body between the engaged position and the released position. This allows a pushing motion towards the centre of the goggles (substantially towards the wearer's head in use) to be used to move the clip from the engaged position to the released position.

Each retaining finger may be bevelled or rounded at its free end. This allows the retaining fingers to move out of the apertures of the tongues in a pivoting motion without being obstructed by the walls of those apertures.

Each retaining finger may include a lip on a back surface of the finger. The lip engages an edge of the aperture of the tongue to prevent the finger from sliding out of the tongue.

Two tongues may be provided on each lateral side of the lens assembly and each moveable clip may include two fingers. This provides a more secure attachment of the lens assembly to the body.

The lens assembly may comprise a lens and a framework bonded to a rear surface of the lens. This allows the tongues to be attached to the lens, as the tongues may be provided as part of the framework. It also provides structural reinforcement to the lens.

The framework may be hidden behind the lens in use. This provides a goggle which is more aerodynamically streamlined and has fewer protruding parts that may catch during an impact. The resulting lens is also aesthetically simpler, having an attractive "frameless" look.

The framework may include at least one tab projecting beyond a lateral edge of the lens. This provides a handle that can be used to pull the lens assembly away from the body once the clips are in the released position. This helps to overcome the attraction of the magnetic elements and easily remove the lens assembly, again bearing in mind that a user may be wearing gloves while swapping over a lens.

The framework may include two tabs projecting beyond each lateral edge of the lens and the actuating portion may be disposed between the tabs when the clip is in the engaged position. This provides a simple and functional arrangement which is highly compact. The lens is removed by pushing on the actuating portion while pulling on the tabs, a motion which is simple and convenient to perform even with a gloved hand.

Magnets may be provided on both of the lens assembly and the body. This provides a strong attraction between the lens assembly and the body, which may be preferred as the lens is less likely to be knocked away from the body.

Magnets may be provided on only one of the lens assembly and the body, and pieces of steel or another magnetic material which are not permanently magnetised are attached to the other of the lens assembly and the body. This provides a less strong attraction between the lens assembly and the body, which may be preferred as it makes the lens assembly easier to remove.

Lugs may be provided on one of the lens assembly and the body, for interfacing with indents or apertures on the other of the lens assembly and the body. The lugs and indents locate the lens assembly on the body and resist lateral movement of the lens assembly.

BRIEF DESCRIPTION OF THE DRAWINGS

For a better understanding of the present invention, and to show more clearly how it may be carried into effect, reference will now be made by way of example only to the accompanying drawings, in which.

DESCRIPTION OF PREFERRED EMBODIMENTS

Figure 1:
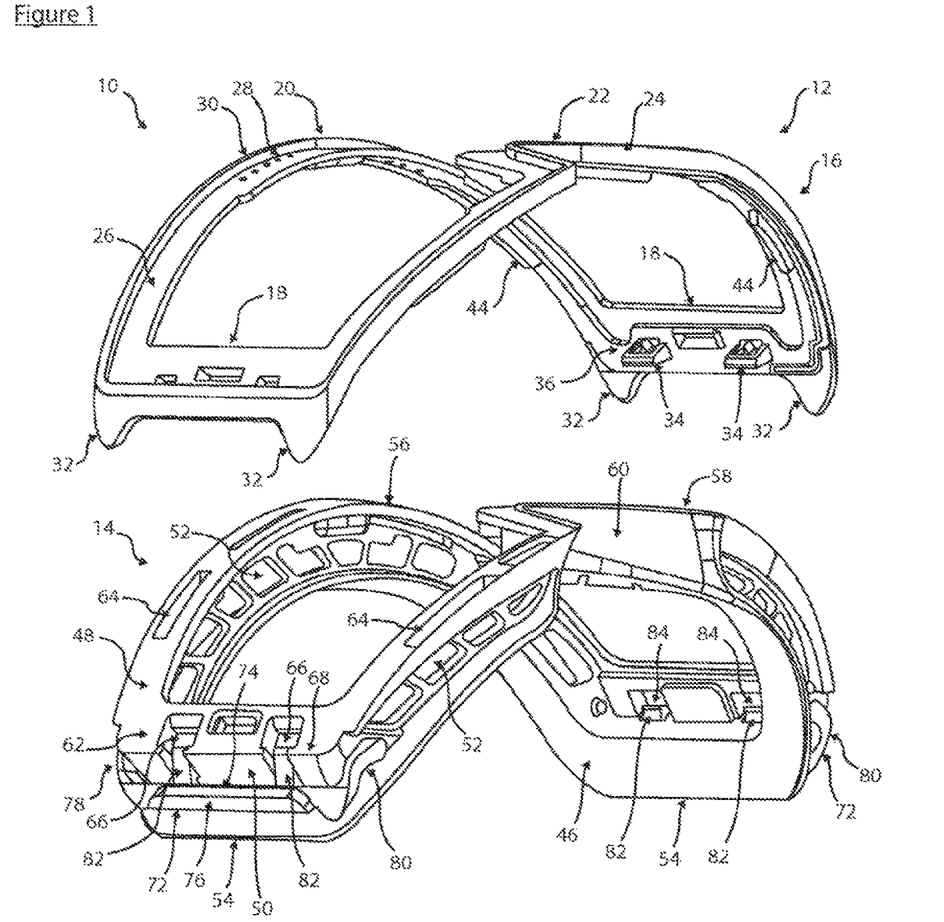
FIG. 1 shows an exploded perspective view of a goggle for use in snowsports, with the lens assembly removed from the body and the lens omitted for clarity.
Figure 2:
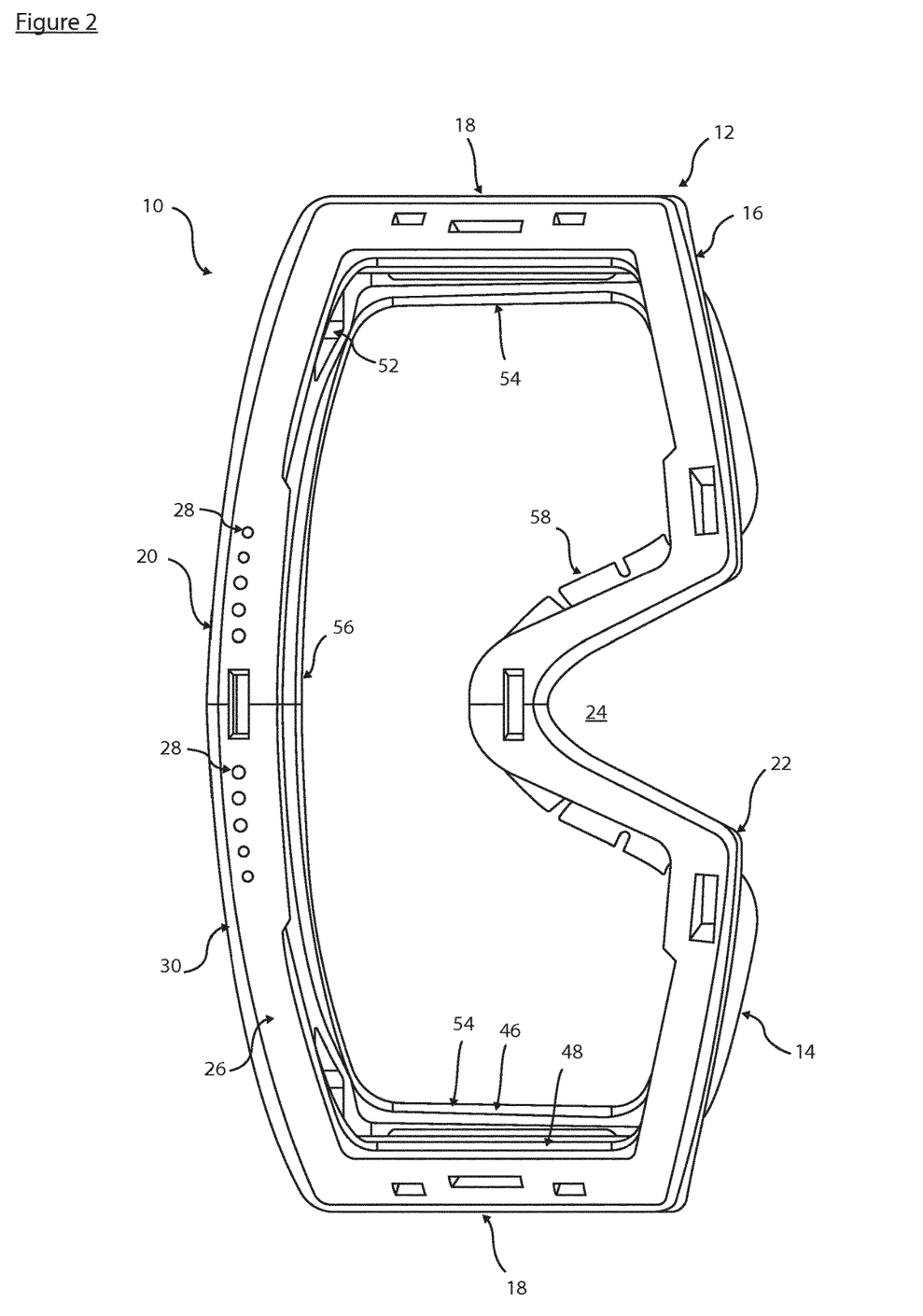
FIG. 2 shows a front view of the goggle of FIG. 1.

Referring firstly to FIGS. 1 and 2, a goggle for use in snowsports is indicated generally at 10. The goggle comprises a lens assembly 12 and a body 14.

The lens assembly 12 includes a framework 16 and a lens, which has been omitted from the drawing for clarity. The framework 16 has the form of an outline of a lens. It is curved to conform to a wearer's head shape. The framework has a pair of lateral sides 18. The lateral sides 18 are parallel. The lateral sides 18 are joined by a forehead bridge 20 and a nose bridge 22. The nose bridge 22 is contoured to define a notch 24 (best seen in FIG. 2) for receiving the wearer's nose. The lateral sides 18, forehead bridge 20 and nose bridge 22 are joined to form a closed loop.

The framework 16 includes a curved front surface 26 for abutting a rear surface of the lens. The front surface 26 is surrounded by a lip 30. The lens sits in front of the framework 16 so that the framework 16 is substantially obscured from view from the front.

Apertures 28 are provided in the front surface 26 extending through the framework 16 for ventilation. Corresponding apertures are provided in the lens. The apertures 28 are provided on the forehead bridge 20. The apertures 28 are provided proximal to the centre of the forehead bridge 20. In this embodiment, two rows of five apertures 28 each are provided. The apertures 28 are circular.

Figure 7:
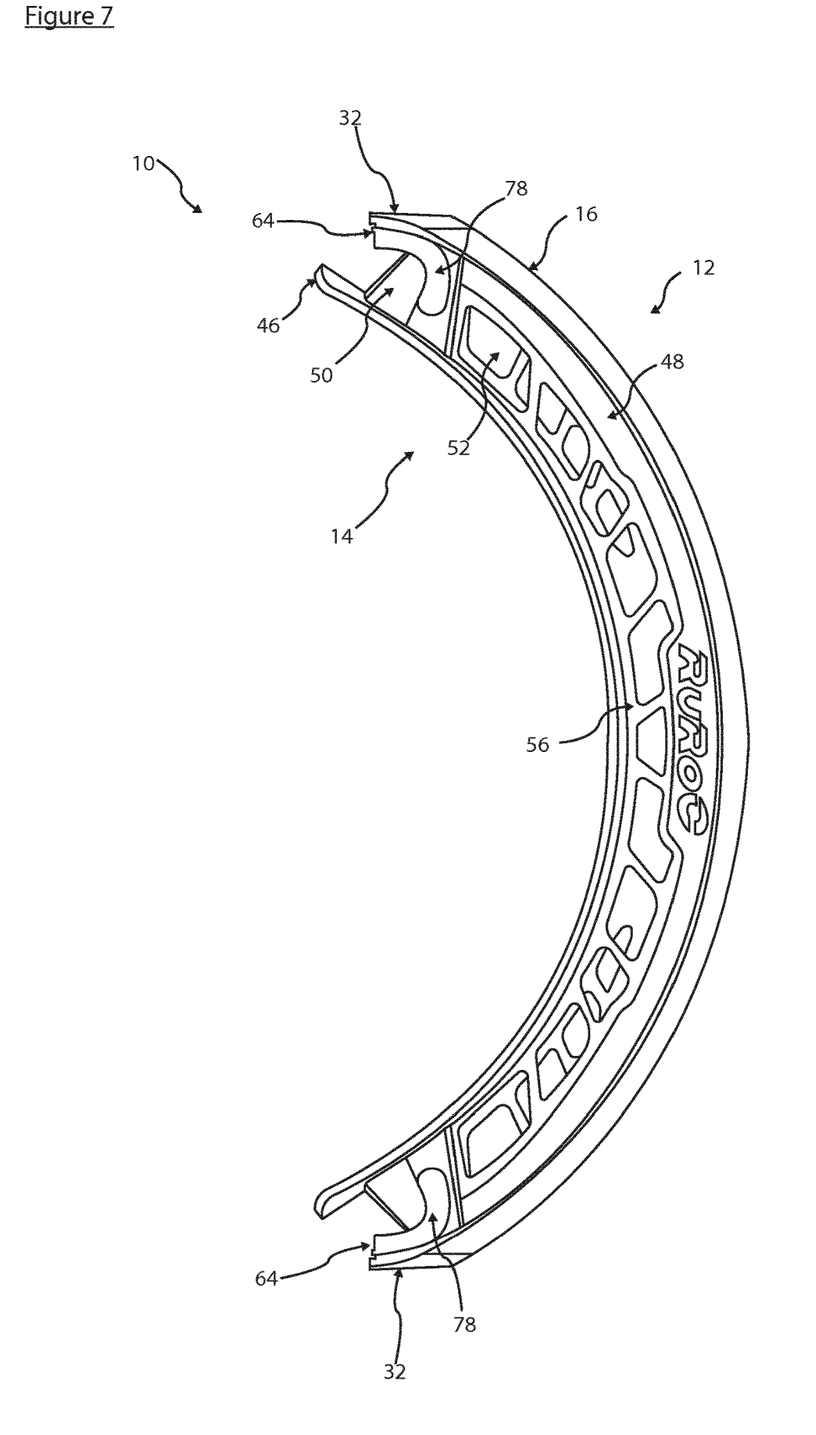
FIG. 7 shows a top view of the goggle of FIG. 1 with the clips in the engaged position.
Figure 8:
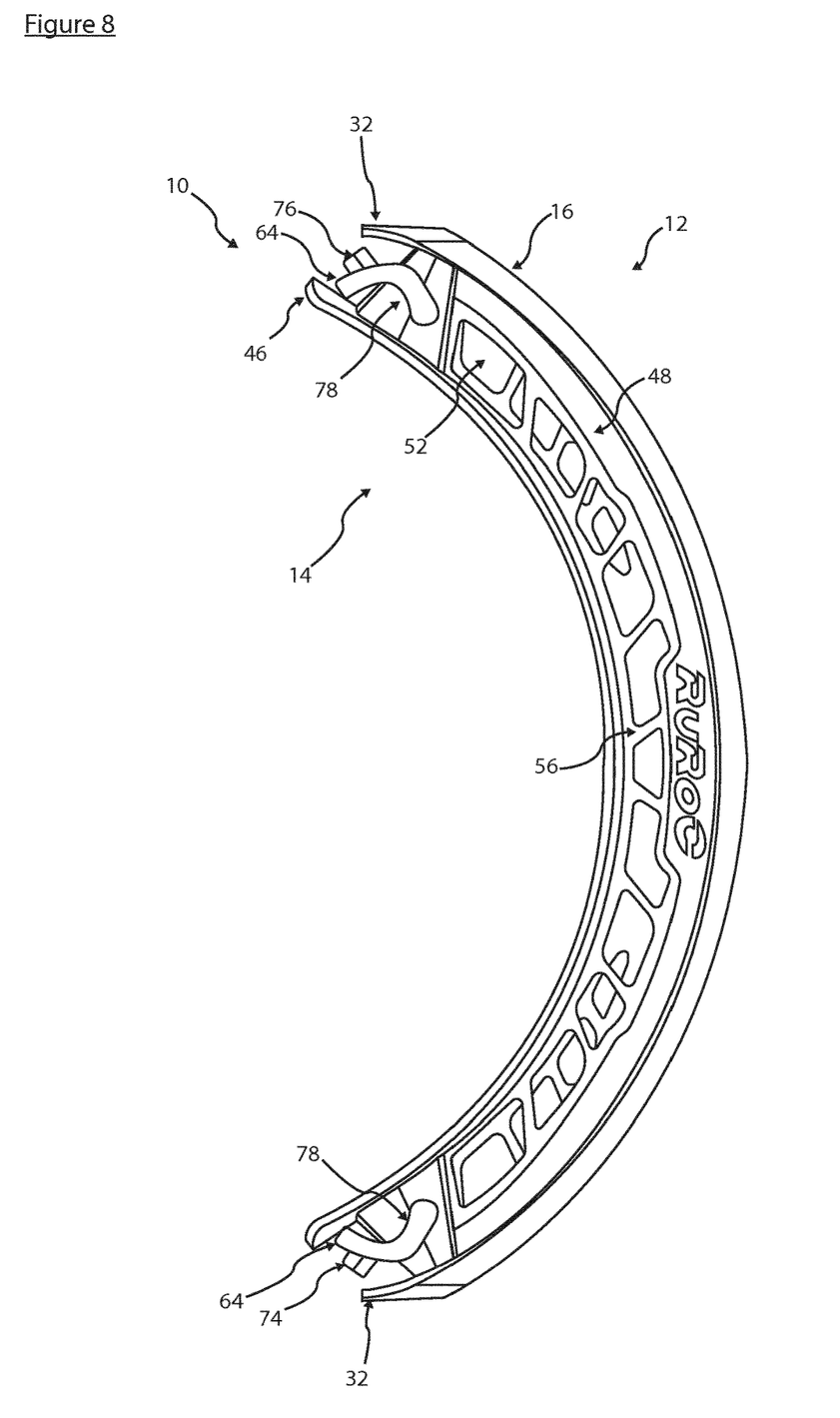
FIG. 8 shows a top view of the goggle of FIG. 1 with the clips in the released position.

Each lateral side 18 of the framework includes a pair of tabs 32. The tabs 32 extend from the lateral sides 18 of the framework 16 and approximately follow and extend the curve of the framework. Each tab 32 is located at a corner of the framework 16. Each tab 32 is tapered so that its thickness (in a direction perpendicular to a tangent plane of the framework) reduces away from the lateral edge of the framework. This is best appreciated in FIGS. 7 and 8.

Each lateral side 18 of the framework includes a pair of tongues 34. Each tongue 34 extends from a rear surface 36 of the framework 16.

Figure 3:
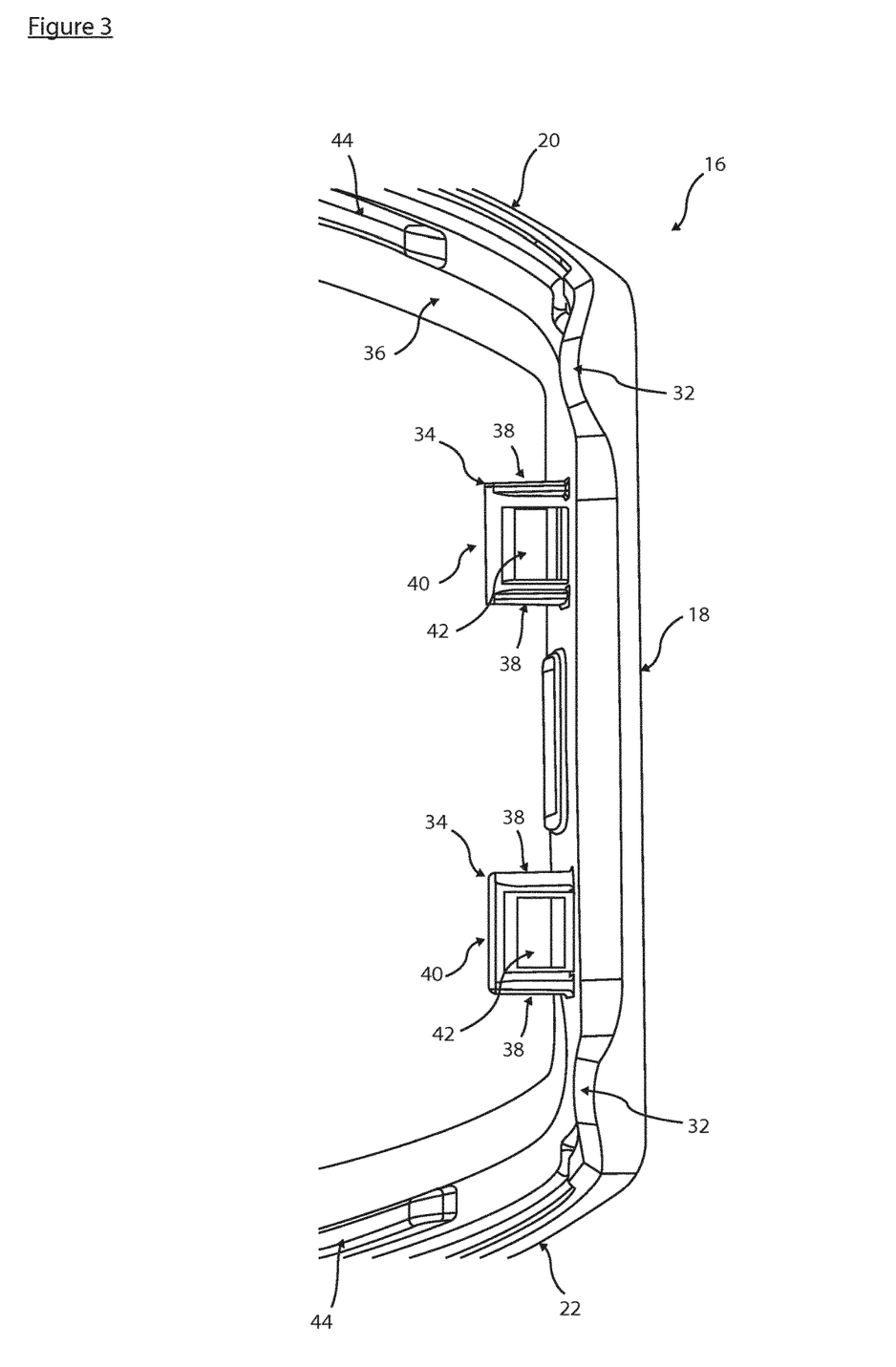
FIG. 3 shows a rear view of part of the framework of the lens assembly of the goggle of FIG. 1.

Referring now to FIG. 3, each tongue 34 is formed of a pair of columns 38 connected to the rear surface 36 of the framework 16 at one end and joined at the other end by a spar 40. Each spar 40 extends in a direction parallel to the lateral sides 18. The columns 38, spar 40 and rear surface 36 define an aperture 42 in each tongue 34. Each aperture 42 passes through the respective tongue in a direction approximately parallel to the curvature of the framework 16.

Lugs 44 are provided on the rear surface 36 of the framework 16. The lugs 44 are elongate protrusions from the rear surface 36. Two lugs 44 are provided on the forehead bridge 20. The lugs 44 are provided substantially midway between the centre of the forehead bridge 20 and the lateral sides 18. Two further lugs 44 are provided on the nose bridge 22. These lugs are situated between the contoured portion of the nose bridge 22 and the lateral sides 18. The lugs 44 are for insertion into indents 64 on the body 14. Referring again to FIG. 1, the body 14 is similar to the framework 16 in that it has the form of an outline of a lens. The body 14 has an overall curvature to conform to a wearer's face.

The body 14 includes a rear flange 46 and a front flange 48. The rear flange 46 and front flange 48 are each curved to conform to the face of a wearer. The rear flange 46 and the front flange 48 are joined by a side wall 50. The rear flange 46, front flange 48 and side wall 50 extend in a loop around the outline of a lens shape to form a pair of lateral sides 54 joined by a forehead bridge 56 and a nose bridge 58. The nose bridge 58 is contoured to define a notch 24 for receiving a wearer's nose The side wall 50 includes a plurality of through-apertures 52 on the forehead bridge 56. The side wall 50 includes a further plurality of through-apertures 52 on the nose bridge 58. The through-apertures 52 provide ventilation and the reduce the weight of the goggle body. The through apertures 52 take up over half of the surface area of the side wall 50 of the forehead bridge 56. In this embodiment and more preferably, the through-apertures 52 take up over 75% of the surface area of the side wall 50 of the forehead bridge 56. For clarity, only one of the through apertures 52 is labelled in the Figures.

The front flange 48 includes a front surface 62 for abutting the rear surface 36 of the framework 16. The front surface 62 of the body 14 includes indents 64 corresponding to each lug 44. The indents 64 are elongate depressions in the front surface 62 of the body 14.

Figure 4:
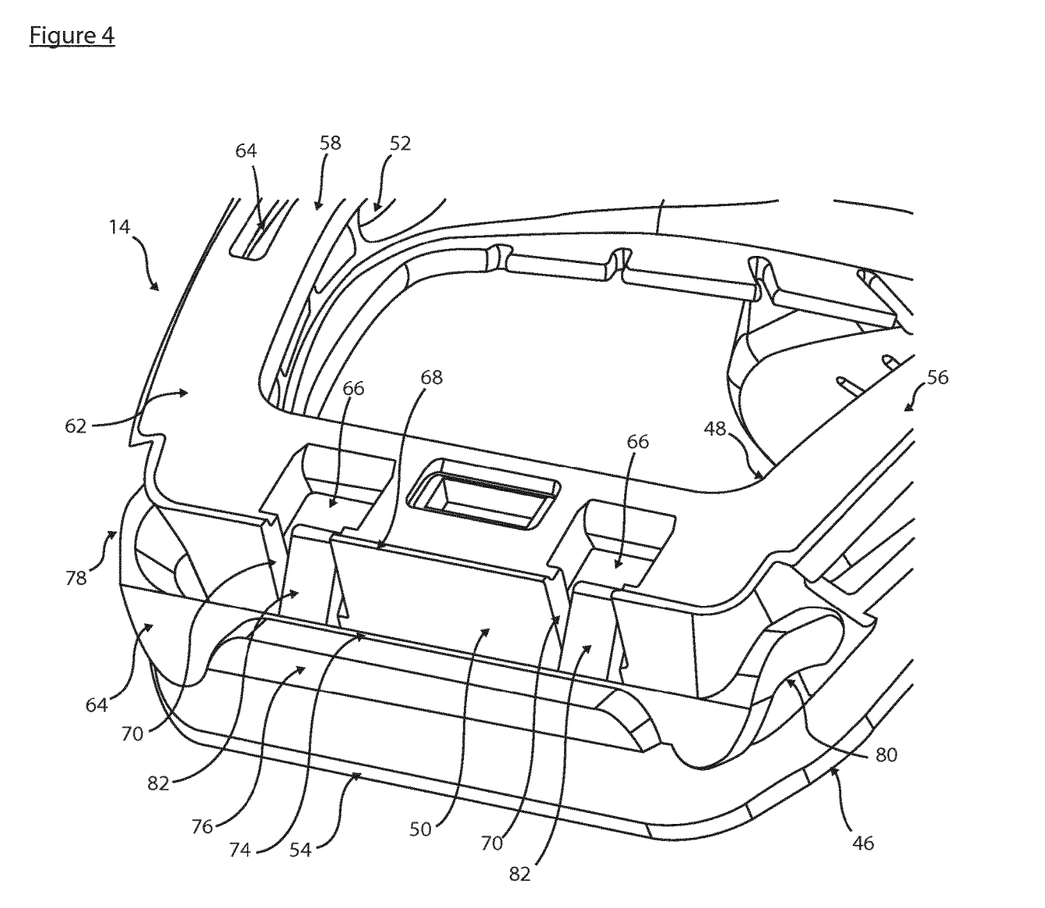
FIG. 4 shows a perspective view of part of the body of the goggle of FIG. 1 with the clips in the released position.
Figure 5:
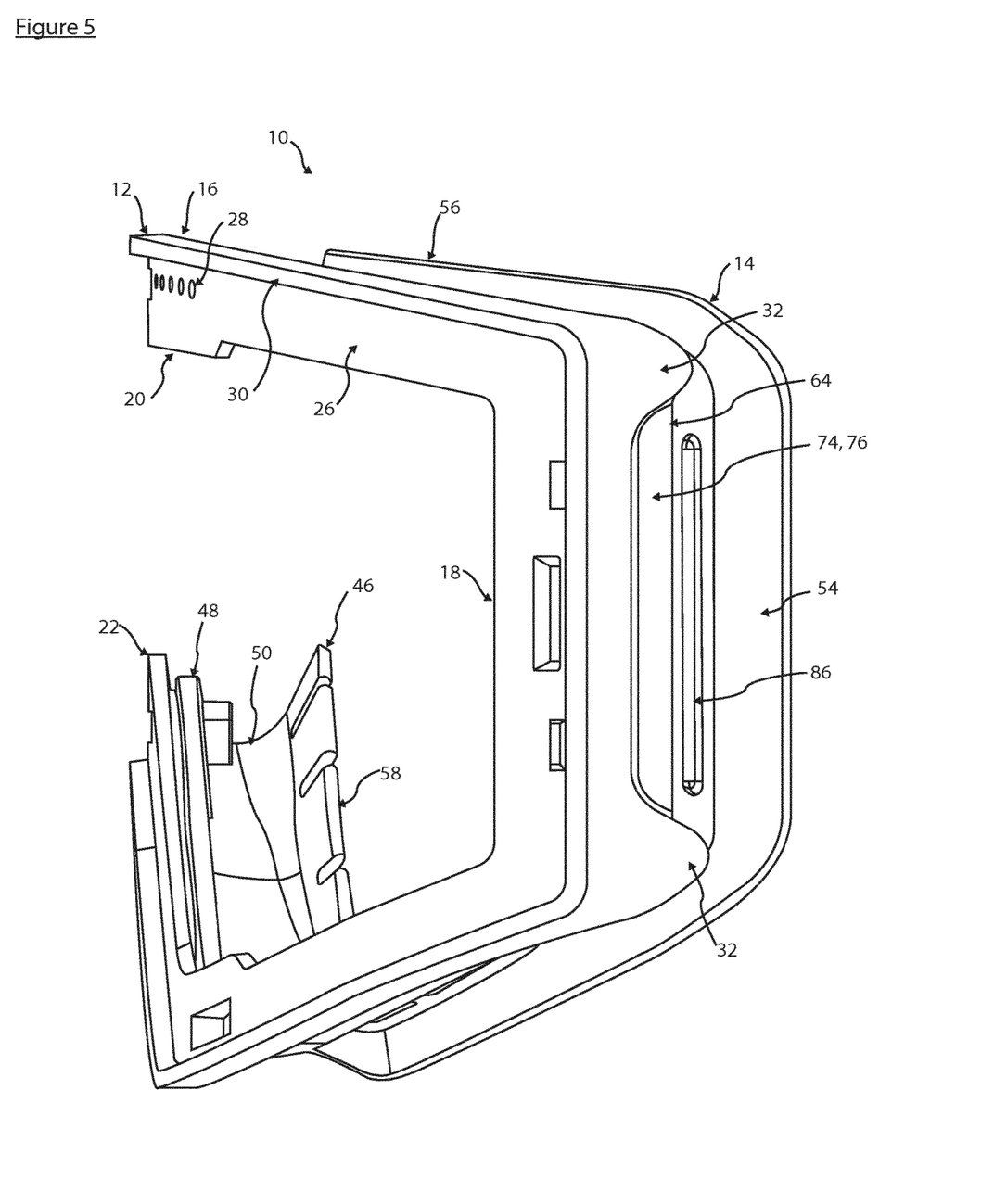
FIG. 5 shows a side view of the goggle of FIG. 1 with the clips in the engaged position.
Figure 6:
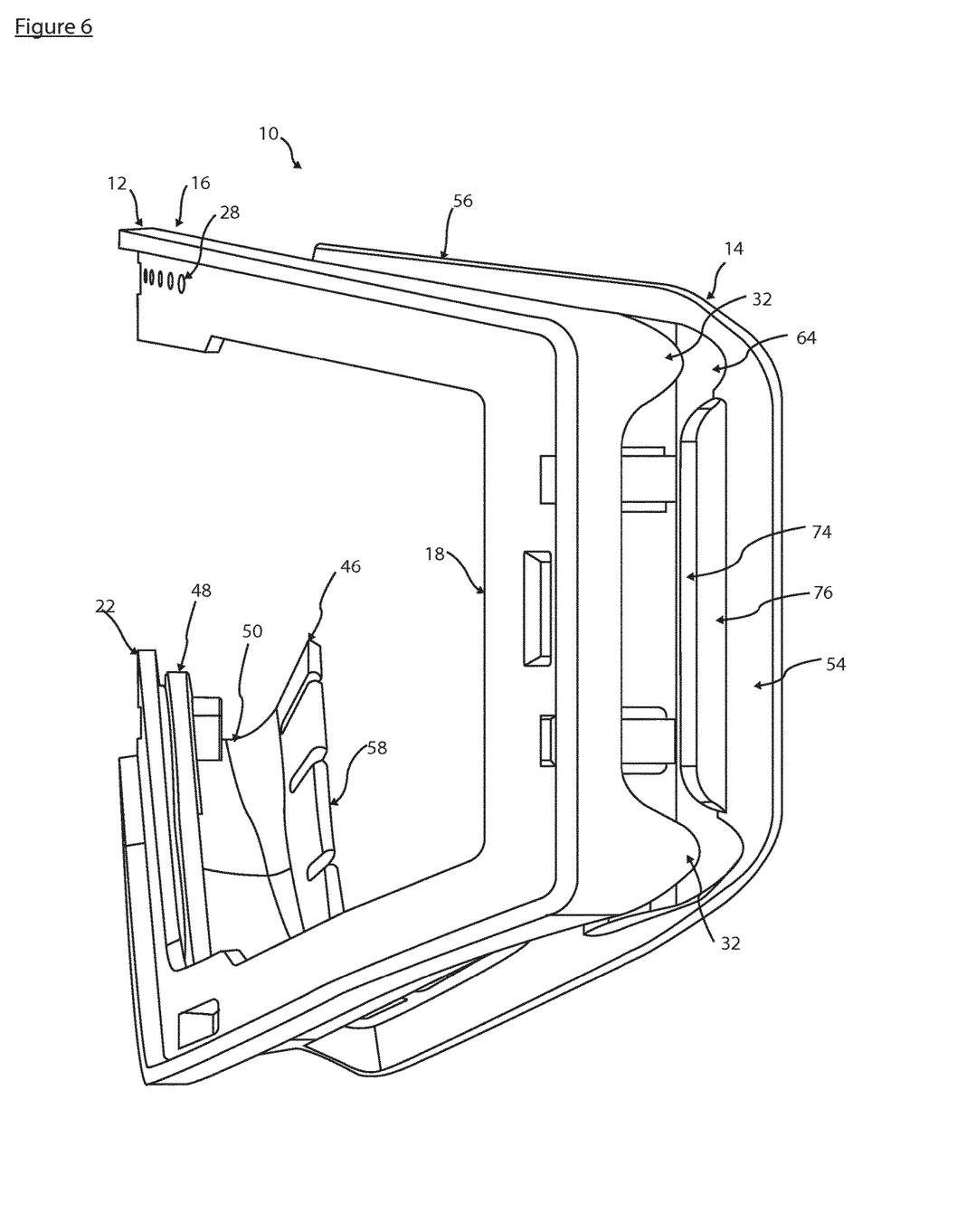
FIG. 6 shows a side view of the goggle of FIG. 1 with the clips in the released position.

The front flange 48 includes a pair of apertures 66 on each of its lateral sides 54. The apertures 66 are sized to receive the tongues 34 snugly. The apertures 66 are open to lateral edges 68 of the front flange 48. The side wall 50 includes a pair of slots 70 (not referenced in FIG. 1 for clarity, see FIG. 4), each extending adjacent the aperture 66 and merging into the aperture to form a continuous approximately L-shaped cut through the side wall 50 and front flange 48.

A clip 72 is provided on each lateral side 54 of the body. The clip 72 includes an elongate bar portion 74 which is disposed parallel to the lateral sides 54. The bar portion 74 extends beyond the lateral part of the side wall 50. An arm 78, 80 extends from each end of the bar portion 74. One arm 78 of each clip 72 is hinged to a point on the side wall of the forehead bridge 56 and the other arm 80 of each clip 72 is hinged to a point on the side wall of the nose bridge 58. Each arm 78, 80 is substantially L-shaped.

The bar portion 74 includes a raised actuation portion 76. The actuation portion 76 is a section of the bar portion 74 which is proud of the rest of the bar portion 74. The actuation portion 76 is disposed in the centre of the bar portion 74.

Figure 1B:
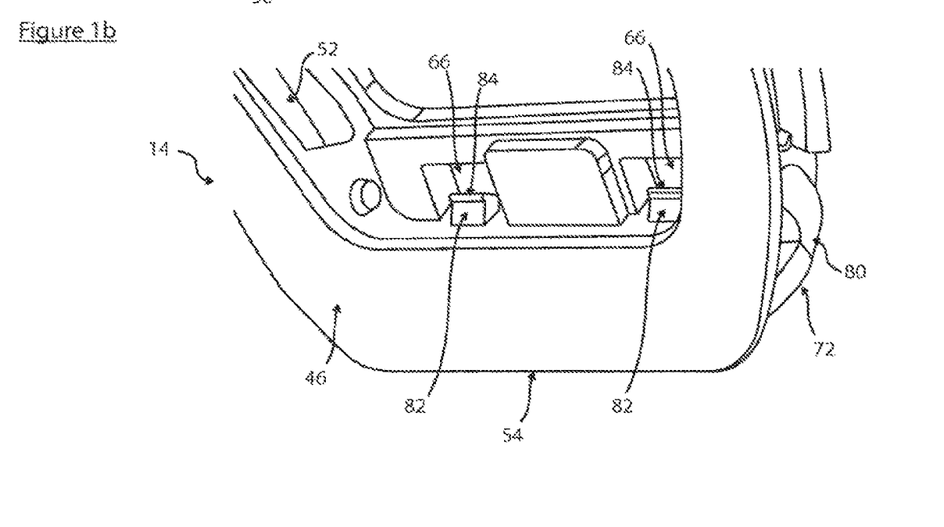
FIG. 1b shows an expanded view of part of the goggle of FIG. 1.

Each clip includes a pair of fingers 82. Each finger 82 extends from the respective bar portion 74. Each finger 82 extends in substantially the same direction as each arm 78, 80. Each finger 82 is rounded on a front edge (front meaning towards the lens and away from the user's head in use). Each finger 82 includes a lip 84 on a rear edge (shown expanded in FIG. 1b).

The clips 72 have an engaged position and a released position. In the released position, the bar portion 74 of each clip is disposed close to the rear flange 46, and the fingers 82 extend just into the slots 70. The fingers extend at an angle of around 45 degrees to the rear flange 46. In the engaged position, the bar portion 74 of each clip is disposed close to the front flange 48 and the fingers 82 extend through the slots 70 and well into the space behind the apertures 66, to engage into the apertures 42 of the tongues 34. In this position the fingers 82 are substantially parallel to the front flange 48. The fingers 82 are situated behind the apertures 66.

A slot 86 is provided in the side wall 50 on each lateral side 54 of the body 14 for receiving a headstrap (not shown).

In use, the lens assembly 12 is attached to the body 14. The rear surface 36 of the framework 16 abuts the front surface 62 of the front flange 48 of the body 14. Each tongue 34 extends into an aperture 66. The clips 72 are in the engaged position and each finger 82 extends into the aperture 42 of one of the tongues 34. A rear surface of each finger 82 engages a front surface of each spar 40. A front surface of each tongue 34, being composed of the front surfaces of the respective spars and columns, bears against a rear wall of each aperture 66. Each actuation portion 76 sits between the respective pair of tabs 32 and is flush with the tabs 32.

These embodiments are provided by way of example only, and various changes and modifications will be apparent to persons skilled in the art without departing from the scope of the present invention as defined by the appended claims.

The invention claimed is:

1. A goggle for use in snowsports, the goggle comprising a body and a detachable lens assembly, magnets or magnetic elements being provided on the lens assembly and magnets or magnetic elements being provided in corresponding positions on the body, for detachably holding the lens assembly to the body, at least one tongue extending from a rear surface of the lens assembly on each of two lateral sides of the lens assembly, each tongue extending in a direction substantially behind the lens assembly, into the body when the lens assembly is fitted to the body, and an aperture extending through each tongue, and at least one clip being provided on each lateral side of the body, each clip being hinged to the body and movable between a released position and an engaged position, each clip including a retaining finger which in the engaged position passes into the aperture in the corresponding tongue, preventing detachment of the lens assembly from the body and in the released position moves clear of the tongue, allowing detachment of the lens assembly, in which each clip comprises an actuating portion for actuating the clip by hand, in which a corresponding aperture is provided in the body for receiving each tongue, each aperture of the body is situated near a lateral edge of the body, and a channel is provided joining each aperture of the body to the respective lateral edge of the body, each channel being open to a front surface of the body for receiving one of the retaining fingers.

2. A goggle as claimed in claim 1, in which a bearing surface is provided on the body for positioning adjacent each tongue.

3. A goggle as claimed in claim 2, in which each retaining finger is situated in one of the apertures of the body when the clip is in the engaged position.

4. A goggle as claimed in claim 1, in which each clip comprises an elongate bar portion disposed parallel to a respective lateral edge of the body.

5. A goggle as claimed in claim 1, in which pushing the actuating portion towards the body of the lens causes the respective clip to move from the engaged position to the released position.

6. A goggle as claimed in claim 1, in which each clip is pivotable about the body between the engaged position and the released position.

7. A goggle as claimed in claim 1, in which each retaining finger is bevelled or rounded at a front edge of a free end of the retaining finger.

8. A goggle as claimed in claim 1, in which each retaining finger includes a lip on a back surface of the retaining finger.

9. A goggle as claimed in claim 1, in which each clip is biased into the engaged position.

10. A goggle as claimed in claim 1, in which two tongues are provided on each of the lateral sides of the lens assembly and each clip includes two retaining fingers.

11. A goggle as claimed in claim 1, in which lugs are provided on one of the lens assembly and the body, for interfacing with indents or apertures on the other of the lens assembly and the body.

12. A goggle for use in snowsports, the goggle comprising a body and a detachable lens assembly, magnets or magnetic elements being provided on the lens assembly and magnets or magnetic elements being provided in corresponding positions on the body, for detachably holding the lens assembly to the body, at least one tongue extending from a rear surface of the lens assembly on each of two lateral sides of the lens assembly, each tongue extending in a direction substantially behind the lens assembly, into the body when the lens assembly is fitted to the body, and an aperture extending through each tongue, and at least one clip being provided on each lateral side of the body, each clip being hinged to the body and movable between a released position and an engaged position, each clip including a retaining finger which in the engaged position passes into the aperture in the corresponding tongue, preventing detachment of the lens assembly from the body and in the released position moves clear of the tongue, allowing detachment of the lens assembly, in which each clip comprises an actuating portion for actuating the clip by hand in which the lens assembly comprises a lens and a framework bonded to a rear surface of the lens, and the framework is hidden behind the lens in use.

13. A goggle as claimed in claim 12, in which the framework includes at least one tab projecting beyond a lateral edge of the lens.

14. A goggle as claimed in claim 13 in which the framework includes two tabs projecting beyond each of two lateral edges of the lens and the actuating portion of each clip is disposed between the tabs when the clip is in the engaged position.

\* \* \* \* \*